United States Patent [19]
Rasmussen et al.

[11] Patent Number: 5,993,935
[45] Date of Patent: Nov. 30, 1999

[54] COVALENTLY REACTIVE PARTICLES INCORPORATED IN A CONTINOUS POROUS MATRIX

[75] Inventors: Jerald K. Rasmussen, Stillwater; Steven M. Heilmann, Afton; Larry R. Krepski, White Bear Lake; Patrick L. Coleman, Minneapolis; Dean S. Milbrath, Stillwater; Margaret M. Walker, Apple Valley; Donald F. Hagen, Woodbury; Paul E. Hansen, Lake Elmo; John C. Campbell, St. Paul, all of Minn.

[73] Assignee: 3M Innovative Properties Company, St. Paul, Minn.

[21] Appl. No.: 07/776,601

[22] Filed: Oct. 11, 1991

[51] Int. Cl.⁶ .................................. B32B 7/00; D04H 1/16
[52] U.S. Cl. ........................... 428/120; 428/163; 428/216; 428/217; 428/219; 428/223; 428/297.1; 264/22; 264/175
[58] Field of Search ..................................... 428/120, 163, 428/216, 217, 219, 223; 264/22, 175

[56] References Cited

U.S. PATENT DOCUMENTS

| | | | |
|---|---|---|---|
| 3,971,373 | 7/1976 | Braun | 128/146.2 |
| 4,102,746 | 7/1978 | Goldberg | 195/63 |
| 4,153,661 | 5/1979 | Ree et al. | 264/122 |
| 4,342,811 | 8/1982 | Lopatin et al. | 428/220 |
| 4,373,519 | 2/1983 | Errede et al. | 128/156 |
| 4,433,024 | 2/1984 | Eian | 428/198 |
| 4,451,619 | 5/1984 | Heilmann et al. | 525/379 |
| 4,460,642 | 7/1984 | Errede et al. | 428/283 |
| 4,539,256 | 9/1985 | Shipman | 428/315.5 |
| 4,550,123 | 10/1985 | Lopatin | 521/64 |
| 4,565,663 | 1/1986 | Errede et al. | 264/120 |
| 4,681,101 | 7/1987 | Bicoll | 128/303 |
| 4,722,898 | 2/1988 | Errede et al. | 435/182 |
| 4,737,560 | 4/1988 | Heilmann et al. | 526/304 |
| 4,757,014 | 7/1988 | Hendrickson et al. | 435/180 |
| 4,810,381 | 3/1989 | Hagen et al. | 210/502.1 |
| 4,855,234 | 8/1989 | Hendrickson et al. | 435/181 |
| 4,868,032 | 9/1989 | Eian et al. | 428/198 |
| 4,871,824 | 10/1989 | Heilmann et al. | 526/304 |
| 4,936,494 | 6/1990 | Hibino et al. | 435/288 |
| 4,957,943 | 9/1990 | McAllister et al. | 521/64 |
| 4,963,431 | 10/1990 | Goldstein et al. | 428/288 |
| 4,971,736 | 11/1990 | Hagen et al. | 264/22 |
| 5,013,795 | 5/1991 | Coleman et al. | 525/279 |
| 5,041,225 | 8/1991 | Norman | 210/500.36 |
| 5,059,654 | 10/1991 | Hou et al. | 525/54.1 |

FOREIGN PATENT DOCUMENTS

| | | |
|---|---|---|
| 0 117 478 | 9/1984 | European Pat. Off. . |
| 0 264 804 | 4/1988 | European Pat. Off. ........ C12N 11/00 |
| 0 392 735 | 4/1990 | European Pat. Off. . |
| 0 392 783 | 4/1990 | European Pat. Off. . |
| 0 443 853 | 1/1991 | European Pat. Off. . |
| 0 441 660 | 2/1991 | European Pat. Off. . |
| 0 420 053 | 4/1991 | European Pat. Off. . |
| WO 92/070640 | 5/1982 | WIPO ............................ B01D 13/00 |
| WO 92/07640 | 5/1982 | WIPO ............................ B01D 13/00 |
| WO 87/00199 | 1/1987 | WIPO . |
| WO 92/07640 | 4/1988 | WIPO ............................ B01D 13/00 |

OTHER PUBLICATIONS

Coleman et al., *J. Chrom.*, 512, 345–363, 1990.

*Primary Examiner*—Jose' G. Dees
*Assistant Examiner*—Kathryne E. Shelborne

[57] ABSTRACT

A composite article is provided having covalently reactive particles incorporated in a continuous, porous matrix. The reactive particles have surfaces of covalently reactive functional groups capable of directly forming covalent chemical bonds with ligands without need for an intermediate activation step. An adduct composite article is also provided comprising a continuous, porous matrix and derivatized particles dispersed therein. The derivatized particles comprise a direct, covalent reaction product of ligand with the covalently reactive particles. Methods of making and using the composite articles and adduct composite articles are also provided. Preferred covalently reactive functional groups are azlactone-functional groups of the formula:

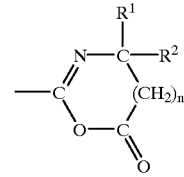

wherein:
  $R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon and 0 to 3 S, N, and nonperoxidic O heteroatoms, or $R^1$ and $R^2$ taken together with the carbon to which they are joined can form a carbocyclic ring containing 4 to 12 ring atoms, and
  n is an integer 0 or 1.

16 Claims, No Drawings

COVALENTLY REACTIVE PARTICLES INCORPORATED IN A CONTINOUS POROUS MATRIX

FIELD OF THE INVENTION

The present invention relates to a composite article comprising covalently reactive particles incorporated in a continuous, porous matrix. Covalently reactive particles have a reactive functional group and are capable of forming a covalent chemical bond to a ligand without the need for an intermediate activation step. The composite article is useful in diagnostic devices, in affinity purifications and enzyme immobilization.

BACKGROUND OF THE INVENTION

Finely divided solids or particles, commonly referred to as fillers, are often added to polymer systems to produce a variety of solid, essentially nonporous, composite materials. Fillers are typically added to polymeric materials for the purposes of either improving physical properties or reducing overall cost. These fillers are primarily inert, unreactive particles, chosen largely according to their compatibility with the matrix polymer and/or their inexpensive nature. Typical of such fillers are minerals, clays, metallic powders, inorganic oxides, glass, talc, wood powder, and carbon black.

Porous, particle-filled composite articles are also known in the art. These materials find use in such applications as filtration or separation media, or in other applications where permeability to gases or liquids is required.

U.S. Pat. No. 4,957,943 describes a microporous particulate-filled thermoplastic polymeric article which may be in the form of a film, a fiber, a hollow fiber, or a tube. The particulate filler is of submicrometer or low micrometer size and may be a metal, a metal oxide, or a carbonaceous material such as carbon black. These composites are useful as protective garments or as X-ray or electromagnetic shielding materials.

U.S. Pat. Nos. 4,550,123 and 4,342,811 describe microporous polymeric fibers and films which contain particles capable of sorbing vapors, liquids, and solutes. Typical sorbent particles include active carbon, silica gel, and molecular filter type materials.

In addition to particulate-filled microporous materials described above, it is also known to incorporate particles into macroporous fibrous webs or sheet materials. For example, U.S. Pat. No. 3,971,373 describes a porous sheet product comprising a web of entangled melt-blown organic polymeric microfibers and a three dimensional array of solid particles uniformly dispersed and physically held in the web. Typical particles are activated carbon or alumina. The composite sheets are useful for adsorbing organic or acidic vapors from an air stream. U.S. Pat. No. 4,963,431 discloses a permeable, nonwoven polymer pad having zeolite particles adhesively bonded throughout the pad. This pad is useful for absorbing ammonia from a fluid.

U.S. Pat. No. 4,153,661 describes a uniformly porous, high void-volume composite sheet comprised of a particle material uniformly distributed throughout a matrix formed of interentangled, fibrillated polytetrafluoroethylene (PTFE) fibrils. The described particles are primarily inorganic particles. U.S. Pat. Nos. 4,373,519 and 4,460,642 describe the incorporation of hydrophilic, organic, water-swellable particles into a fibrillated PTFE matrix. Preferred composites contain particles of crosslinked dextran and are useful as a wound dressing. U.S. Pat. No. 4,810,381 discloses a composite chromatographic article comprising a PTFE fibril matrix and a non-swellable sorptive particle enmeshed in the matrix. Preferred particles are inorganic oxides such as silica and zirconia.

The immobilization of proteins or enzymes on insoluble, solid supports has long been recognized as being desirable. Immobilization allows easy recovery and reuse, and often enhances stability, of biologically active molecules. Methods of immobilization range from physical adsorption, to physical entrapment, to ionic or covalent bonding of the biologically active molecule to the support.

U.S. Pat. No. 4,855,234 discloses a composite article provided by subjecting a fibrous support in sequence to a surface modification treatment, a coating of a protein immobilizer compound, and a biologically active protein. U.S. Pat. No. 4,963,494 describes an ultrafiltration membrane having an enzyme immobilized thereon. Immobilization is accomplished by impregnating a membrane with a solution of a water-soluble polymer, utilizing a crosslinking agent to crosslink the polymer within the pores of the membrane, then covalently binding the enzyme to the membrane through functional groups of the crosslinked polymer.

U.S. Pat. No. 4,102,746 discloses proteins such as enzymes immobilized on a microporous binder or matrix having finely divided filler particles dispersed throughout the binder. Proteins are covalently coupled via a chemical bond to dispersed filler particles in the microporous material, using bridging agents in a two-step procedure.

U.S. Pat. No. 5,041,225 discloses a hydrophilic, semipermeable membrane of PTFE having internal and external surfaces coated with a complex of a hydrophilic polymer which adheres to the membrane structure and a complexing agent. The complex renders the PTFE membrane hydrophilic and protein affinitive. Preferred complexing agents are boric acid, sodium borate, or sodium chloride.

SUMMARY OF THE INVENTION

What the art needs is a composite article which combines a continuous, porous matrix with particles which are directly covalently reactive with ligands, without intermediate activation steps such as those required in U.S. Pat. No. 4,102,746. Such directly covalently reactive particles incorporated in a continuous, porous matrix combine facility of ligand derivatization of such particles in a simplified procedure with substantial assurance of covalent coupling of the ligand on the reactive particles incorporated in the porous matrix for further chemical or biological interaction.

Briefly, the present invention a composite article comprises covalently reactive particles incorporated within a continuous, porous matrix. The reactive particles have surfaces comprising covalently reactive functional groups capable of directly forming covalent chemical bonds with ligands without need for an intermediate activation step. In another aspect, the present invention provides an adduct composite article, comprising a continuous, porous matrix and derivatized particles dispersed therein. The derivatized particles comprise a direct, covalent reaction product of ligand with reactive particles having surfaces comprising covalently reactive functional groups capable of directly forming covalent chemical bonds with said ligands without need for an intermediate activation step. In a particularly preferred aspect of the present invention, the ligand is a biologically active material. In this aspect, the present invention therefore provides a composite article comprising biologically active material covalently immobilized to particles dispersed within a continuous, porous matrix.

The invention provides a composite material useful in at least diagnostics devices, in affinity purifications, or in enzyme immobilization.

In another aspect, the invention provides a method for providing a composite article described above comprising the steps of providing a material useful for the preparation of a continuous, porous matrix; forming a continuous, porous matrix from the material; incorporating reactive particles within the matrix to provide the composite article. Incorporation of particles in the matrix can be accomplished either by dispersing the particles within the matrix during the matrix-forming process, or intimately mixing the particle with the matrix-forming material prior to the matrix-forming process. The method further comprises covalently coupling a ligand to the reactive particles by direct covalent chemical bonds either prior to the matrix-forming process or after the matrix-forming process.

In yet another aspect, the invention provides a method for purifying an analyte in a fluid, comprising the steps of providing an adduct composite article described above; exposing said adduct composite article to the fluid comprising the analyte which has an affinity for ligand such that the analyte physically binds to the ligand; washing the composite article so as to remove all non-analyte materials; and recovering the analyte from the composite article.

A feature of the present invention is that the composite article has reactive particles dispersed, preferably substantially uniformly, in a continuous, porous matrix which can be directly derivatized with a ligand by covalent coupling.

Another feature of the present invention is that the composite article can be rendered biologically active by direct covalent coupling of a biologically active material as a ligand to reactive particles. This direct covalent coupling reduces incidence of biologically active material leaching from or becoming inactive on the reactive particles.

An advantage of the present invention is that reactive particles of the composite article can determine biological or chemical interaction with analytes in a fluid while the continuous, porous matrix enables physical interaction with such analytes in the fluid.

EMBODIMENTS OF THE INVENTION

A composite article of the present invention is a continuous, porous matrix having dispersed therein directly covalently reactive particles. The particles are directly covalently reactive because reactive functional groups capable of forming a covalent chemical bond to a ligand are present on internal and/or external surfaces thereof.

Directly Covalently Reactive Particles

Particles which are directly covalently reactive with ligands can vary widely within the scope of the present invention. Such particles have at least one reactive functional group capable of forming a covalent chemical bond to a ligand by direct interaction. Thus, the ligand becomes chemically coupled to the particle (and thus to the composite article) rather than being physically bound (sorbed, adsorbed, absorbed, etc.) as occurs with many particle-loaded composites articles previously known.

A necessary characteristic of a reactive functional group useful in the present invention is that it can form a covalent chemical bond by direct interaction with the ligand, i.e., without the need for an intermediate activation step. This characteristic obviates the need for chemical modification of the particle-loaded matrix by the use of, for example, bridging agents disclosed in U.S. Pat. No. 4,102,746 (such as gamma-aminopropyltriethoxysilane or polyethylenimine) as well as eliminates the need for activating the functionality of the particle loaded matrix (or bridging agent treated matrix) by means of a bifunctional electrophilic agent disclosed in U.S. Pat. No. 4,102,746 (such as glutaraldehyde or bisimidate esters) or other activating chemistries such as carbodiimides and acid halides which are common in the art. Thus, reactive particles useful in the present invention having directly covalently reactive functional groups greatly simplifies the procedures needed to covalently couple a ligand to the composite and allows for a more uniform and controlled covalent coupling to be accomplished.

The reactive particles useful in the present invention are generally of two broad types: chemically modified inorganic particles and organic, polymeric particles. The inorganic particles may be, for example, metals; metal oxides such as alumina, silica, and zirconia; glass beads, glass bubbles, and controlled pore glass; and the like. These particles are chemically modified such as by coating with a polymer (usually organic) which contains a reactive functional group or by reaction with a suitable reagent (e.g. an alkoxy silane coupling agent) containing the reactive functional group. The organic particles may be crosslinked or noncrosslinked polymers which have been prepared, for example, by polymerization or copolymerization of a monomer containing the appropriate reactive functional group, by coating a particle support as described above, or by chemical modification of another polymer to introduce the reactive functional group. A number of useful particles are commercially available or can be prepared by techniques well known in the art, a partial listing of which can be found below in Table A.

Reactive particles useful in the present invention can have a spherical shape, a regular shape, or an irregular shape. Size of reactive particles can vary widely within the scope of the invention and will depend to some extent upon the type of continuous, porous matrix into which such particles are incorporated. Generally size of reactive particles ranges from 0.1 micrometers to 5 millimeters in average diameter.

The directly covalently reactive functional groups which are useful for the purposes of the invention can be classified in general as electrophiles. Reaction with a nucleophile (e.g. amine, alcohol, or mercaptan) produces a covalent chemical bond either by an addition reaction or by a displacement or substitution type reaction (in which a byproduct molecule is released). Addition type reactions are preferred. Examples of useful reactive functional groups and of commercially available particles containing them are listed in Table A.

TABLE A

Functional Groups and Particles
For Porous Composite Articles

| Functional Group | Trade Name | Supplier | Type |
|---|---|---|---|
| Epoxide or Oxirane: | Eupergit ™ | Rohm Pharma | Methacrylamide copolymer |
| | Toraysphere ™ | Toray | Methacrylate copolyiner |

TABLE A-continued

Functional Groups and Particles
For Porous Composite Articles

| Functional Group | Trade Name | Supplier | Type |
|---|---|---|---|
| | ImmunoPure ™ | Pierce | Agarose |
| | Hydropore-EP ™ | Rainin | Silica |
| | BIOSYNTH* ™ | Crescent | Vinyl acetate copolymer |
| N-Hydroxysuccinimide Esters: | Affi-Gel ™ | BioRad | Agarose |
| | Affi-Prep ™ | BioRad | Organic polymer |
| Sulfonyl Esters: | Tresyl Activated Agarose | Pierce | Agarose |
| | Tosyl Activated Agarose | Pierce | Agarose |
| Iodoacetyl: | SulfoLink ™ | Pierce | Agarose |
| Aldehyde: | AminoLink ™ | Pierce | Agarose |
| Imidazolyl Carbamate: | Reacti-Gel ™ | Pierce | Agarose |
| | | | Acrylamide Copolymer |
| | | | Siliica |

Particularly preferred as reactive particles useful in the present invention are particles having azlactone-functional groups on internal and/or external surfaces of such particles. Thus, such reactive particles have an azlactone-functional group of Formula I:

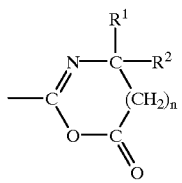

Formula I wherein:
R$^1$ and R$^2$ independently can be an alkyl group having 1 to 14 carbon atoms, a cycloalkyl group having 3 to 14 carbon atoms, an aryl group having 5 to 12 ring atoms, an arenyl group having 6 to 26 carbon and 0 to 3 S, N, and nonperoxidic O heteroatoms, or R$^1$ and R$^2$ taken together with the carbon to which they are joined can form a carbocyclic ring containing 4 to 12 ring atoms, and n is an integer 0 or 1.

Azlactone-functional reactive particles are particularly preferred in the present invention because such particles directly covalently couple ligands better than commercially available reactive functional groups shown in Table A. Further, such azlactone-functional groups are quite stable prior to covalent coupling with a ligand. Further, covalent coupling of a ligand with an azlactone-functional group causes no displacement of a byproduct molecule, which avoids undesired purification of the composite article after covalent coupling of the ligand.

Also, azlactone-functional groups are known to possess high covalent coupling capacities with biologically active materials such as Protein A. Further, such high covalent coupling capacities with Protein A also yield high specific bound biological activity of Protein A as the coupled ligand. Thus, an azlactone-functional reactive particle is particularly preferred for composite articles of the present invention.

Azlactone-functional polymeric particles can be made, for example, by copolymerization of a (meth)acryloylamino acid with a variety of other free radically polymerizable comonomers followed by reaction with a cyclizing agent, as described in U.S. Pat. Nos. 4,737,560 and 4,871,824, which are incorporated herein by reference, or by copolymerization of an alkenyl azlactone with other comonomers as described in assignee's copending patent application U.S. Ser. No. 158,258, filed Feb. 19, 1988, or in counterpart European Patent Publication 0 392 735, which are both incorporated herein by reference. Azlactone-functional particles can also be prepared by solution coating an azlactone-functional polymer onto an organic or inorganic particle, also as described in above mentioned European Patent Publication 0 392 735.

Azlactone-functional reactive particles can also be made from azlactone graft copolymers which are disclosed in U.S. Pat. No. 5,013,795 and European Patent Publication 0 392 783, the disclosures of which are incorporated by reference.

Size of particles of azlactone-functional particles can be from about 0.1 to 1,000 micrometers and preferably from 0.5 to 100 micrometers. Azlactone-functional particles can be porous or non-porous. When porous, the average pore size of the dry azlactone-functional particles can range from about 1 to about 3,000 Angstroms and preferably from 10 to about 500 Angstroms.

Continuous, Porous Matrix

Selection of a continuous, porous matrix can vary widely within the scope of the invention. Useful matrices include woven and nonwoven webs (such as fibrous webs), microporous fibers, and microporous membranes.

Woven and nonwoven webs are useful as matrices for the incorporation of directly covalently reactive particles to form composite articles of the present invention.

Fibrous webs are particularly desired because such webs provide large surface areas, with nonwoven fibrous webs being preferred due to ease of manufacture, low material cost, and allowance for variation in fiber texture and fiber density. A wide variety of fiber diameters, e.g., 0.05 to 50 micrometers, can be used in the preparation of the composite articles of the present invention. Web thickness can be varied widely to fit the end use application, e.g., 0.2 micrometer to 100 cm thick or more.

Fibrous webs incorporating directly covalently reactive particles can be prepared by methods known in the art, or by modifications of methods known in the art. The present invention unexpectedly finds that the reactive functional groups can survive the web making process. Composite articles of the present invention comprising nonwoven webs can be prepared by melt-blowing as is known to those skilled in the art and disclosed in, for example, U.S. Pat. No.

3,971,373, which is incorporated herein by reference. In general, a molten polymeric material is extruded in such a way as to produce a stream of melt blown polymer microfibers. Reactive particles are introduced into the stream of microfibers and become intermixed with these fibers. The mixture of fibers and particles is collected on a collection screen, with the microfibers forming a web and the particles becoming dispersed, preferably substantially uniformly, in the web.

The web optionally can be molded or pressed at a pressure of up to 90 psi to provide an article having a Gurley number of at least 2 seconds, as described in assignee's copending, co-filed application (# 47748U.S.A. 5A), incorporated by reference herein.

The nonwoven composite webs can also optionally include a permeable support fabric laminated to one or both sides of the web, as described in U.S. Pat. No. 4,433,024, or can additionally contain reinforcing fibers as described in U.S. Pat. Nos. 4,681,801 and 4,868,032, all of which patents are incorporated by reference herein.

Reactive particles can also be incorporated into woven or nonwoven webs by impregnating a preformed web with a liquid slurry containing particles, optionally in the presence of an adhesive or binder, then drying to remove the liquid from the composite article. One such method has been described in U.S. Pat. No. 4,963,431, the disclosure of which is incorporated by reference herein.

The preferred materials useful to prepare nonwoven fibrous web for composite articles of the present invention include polymers and copolymers of monomers which form fibrous webs. Suitable polymers include polyalkylenes such as polyethylene and polypropylene, polyvinyl chloride, polyamides such as the various nylons, polystyrenes, polyarylsulfones, polyvinyl alcohol, polybutylene, ethyl vinyl acetate, polyacrylates such as polymethyl methacrylate, polycarbonate, cellulosics such as cellulose acetate butyrate, polyesters such as poly(ethylene terephthalate), polyimides, and polyurethanes such as polyether polyurethanes, and combinations thereof.

Nonwoven webs can also be prepared from combinations of co-extruded polymers such as polyester and polyalkylenes. Copolymers of the monomers which provide the above-described polymers are also included within the scope of the present invention.

Nonwoven webs can also be combined webs which are an intimate blend of fine fibers and crimped staple fibers.

Composite articles of the invention can also be prepared from a porous fibrillated polymer matrix, e.g. fibrillated PTFE, having incorporated or enmeshed therein reactive particles by methods disclosed in, for example, U.S. Pat. Nos. 4,153,661, 4,565,663, 4,810,381, and 4,971,736, all of which are incorporated herein by reference. In general, these methods involve blending reactive particles with a polytetrafluoroethylene dispersion to obtain a putty-like mass, subjecting the putty-like mass to intensive mixing at a temperature between 5° C. and 100° C. to cause fibrillation of the PTFE, biaxially calendering the putty-like mass, and drying the resultant sheet. For example, methods disclosed in U.S. Pat. No. 4,565,663 are useful with provision for the use of isopropanol or tert-butanol as solvents for preferred azlactone-functional reactive particles. Use of ethanol can hydrolyze azlactone-functionality, as described in Comparative Example 1 below.

Reactive particles can also be incorporated into microporous films, fibers, hollow fibers, or tubes by techniques which are known in the art. A preferred technique useful for preparation of microporous thermoplastic polymeric composite articles of the present invention involves dispersing the reactive particle in a liquid to form a colloidal suspension, melt blending a thermoplastic polymer with the colloidal suspension at a temperature sufficient to form a homogeneous solution containing dispersed reactive particles, forming an article from the solution into a desired shape, cooling the shaped article so as to induce phase separation of the liquid and the polymer and to ultimately solidify the polymer, and removing at least a substantial portion of the liquid leaving the particle dispersed within the resultant microporous polymer matrix. This method is described in detail in U.S. Pat. No. 4,957,943, which is incorporated herein by reference.

Alternatively, composite articles of the present invention can also be prepared by thermally induced phase separation techniques, such as disclosed in U.S. Pat. No. 4,539,256, the disclosure of which is incorporated by reference. In such techniques, reactive particles are included in a dispersion of a polyolefin which is heated and stirred to obtain a homogeneous mixture prior to casting the molten mixture onto a heated plate subjected to pressure and an ice water plunge.

Incorporation of Reactive Particles Into a Matrix

The amount of reactive particles incorporated into the continuous, porous matrix can vary widely within the scope of the present invention. Generally, the amount of reactive particle can range from about 1 to 99% by volume of the material comprising the composite article. Preferably, the amount is greater than 20% by volume, and more preferably greater than 50% by volume. Thus, a composite article of the present invention can contain up to 95% or more by weight of reactive particles, thereby providing a potentially high capacity for ligand covalent coupling.

As indicated above, the size of reactive particles can vary from about 0.1 micrometer to 5 millimeters in average diameter. Preferred size ranges, however, depend upon the type of matrix in which reactive particles are incorporated. For example, nonwoven fibrous webs and fibrillated polymer matrices can be formulated with the entire size range of particles. Preferably, about 40–200 micrometers sized particles are preferred for the nonwovens while 1–100 micrometer sized particles are preferred for fibrillated PTFE matrices. For microporous composite articles such as those prepared according to the disclosure of U.S. Pat. No. 4,957,943, much smaller particles, in the range of 0.1 to 20 micrometers, preferably 0.5 to 3 micrometers, and most preferably 0.5 to 1 micrometer, are useful. Occasionally, larger particles can be utilized if they can become reduced to the desired particle size during the formation of the various dispersions according to methods described above. Ultimately, differences in useful particle sizes are dictated by the processes and equipment which are utilized to form the continuous, porous matrix and the porosity of the matrix so formed.

In addition, certain adjuvants may be added to the composite articles of the present invention to include nonreactive particles and fillers, processing aids, surfactants, slip agents, and the like. The desirability and methods of incorporation of such adjuvants into a continuous, porous matrix is described in greater detail in the above referenced and incorporated patents describing formation of matrices useful for the present invention.

Ligands and Adduct Composite Articles

In another aspect of the present invention, composite articles can become adduct composite articles. Adduct composite articles have derivatized particles of ligands which are covalently coupled to such particles to form biologically or chemically active particles. Such derivatized particles can be incorporated into a matrix when forming the matrix according to the methods described above. Alternatively, reactive particles can be derivatized after such reactive particles are incorporated into the matrix.

As stated above, reactive functional groups useful in the present invention are electrophiles. Thus, for direct, covalent coupling, ligands useful in the present invention are nucleophiles. Nonlimiting examples include primary and secondary amines, alcohols, and mercaptans. Of these, amine-functional ligands are especially preferred.

Ligands useful for the preparation of adduct composite articles can also vary widely within the scope of the present invention. Preferably, a ligand is chosen based upon the contemplated end use of the adduct composite article.

Once ligands are covalently coupled to reactive particles and incorporated into a continuous, porous matrix to form an adduct composite article, such ligands are available for biological or chemical interaction, such as adsorbing, complexing, catalysis, or reagent end use.

Adduct composite articles are useful as adsorbants, complexing agents, catalysts, reagents, as enzyme and other protein-bearing supports, and as chromatographic articles.

In a preferred aspect of the present invention, the ligand desired for covalent coupling is a biologically active material having nucleophilic-functional groups. Nonlimiting examples of biologically active materials are substances which are biologically, immunochemically, physiologically, or pharmaceutically active. Examples of biologically active materials include proteins, peptides, polypeptides, antibodies, antigenic substances, enzymes, cofactors, inhibitors, lectins, hormones, receptors, coagulation factors, amino acids, histones, vitamins, drugs, cell surface markers, and substances which interact with them.

Of the biologically active materials, proteins, enzymes and antigenic substances are desired for covalent coupling to reactive particles. Nonlimiting examples of proteins, enzymes, and antigenic substances include natural and recombinant Protein A (ProtA), Immunoglobulins such as rat (rIgG), human (hIgG), bovine (bIgG), rabbit (rbIgG), and mouse (mIgG), Concanavalin A (ConA), Bovine Serum Albumin (BSA), Thyroglobulin (TG), Apoferritin (Af), Lysozyme (Ly), Carbonic Anhydrase (CA), and Bacterial Antigen (BA). Uses for immobilized proteins, enzymes and antigenic substances are disclosed in European Patent Publication 0 392 735.

The presently preferred biologically active material is ProtA because of its multitude of uses in bioseparations.

Alternatively, an adduct composite article of the present invention can comprise a covalently coupled enzyme to catalyze a chemical transformation of substances recognized by the enzyme. Also, a composite article comprising a covalently coupled antigenic substance can be utilized for affinity purification of a corresponding antibody from a complex biological fluid flowing through the porous matrix of the adduct composite article. In another example, porous particles having Protein A covalently coupled to internal and external surfaces of the porous matrix of the adduct composite article can adsorb biologically active materials such as Immunoglobulin G for affinity separations processes. In another example, a composite article can be used for immobilization of antibodies or be used for immunodiagnostics or for Western blotting.

Presently preferred azlactone-functional groups will undergo nucleophilic attack by amines, thiols, and alcohols. Thus, ligands having at least one amine, thiol, or alcohol group thereon are candidates for covalent coupling in an azlactone-functional composite article.

Covalent coupling of ligands to preferred azlactone-functional particles can use methods of using inorganic or organic polyanimic salts in such concentrations as to achieve high bound specific biological activity for the coupled ligand, such as methods disclosed in U.S. patent application Ser. No. 07/609,436, the disclosure of which is incorporated by reference.

Covalent coupling of ligands to preferred azlactone-functional particles according to the present invention results in adduct composite articles having the formula

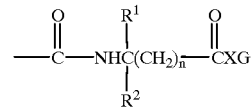

wherein
$R^1$, $R^2$, and n are as previously defined,
X can be —O—, —S—, —NH—, or —NR$^4$ wherein $R^4$ can be alkyl or aryl, and
G is the residue of HXG which performs the adsorbing, complexing, catalyzing, separating, or reagent function of the adduct composite articles.
HXG can be biologically active material.

Ligands having amine, alcohol, or mercapto nucleophilic functional groups react, either in the presence or absence of suitable catalysts, with azlactone-functional groups by nucleophilic addition as depicted in equation (2) below.

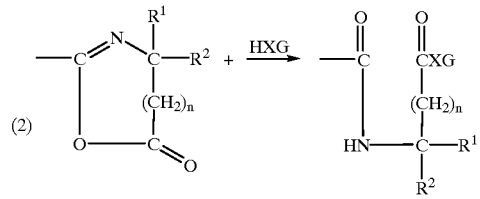

(2)

wherein
$R^1$, $R^2$, n, X, and G are as previously defined.
Depending on the functional group present in the ligand, catalysts may be required to achieve effective attaching reaction rates. Primary amine functional groups require no catalysts. Acid catalysts such as trifluoroacetic acid, ethanesulfonic acid, toluenesulfonic acid, and the like are effective with hydroxy and secondary amine functional groups.

In other aspects of the invention, the ligand is not biologically active but has other properties which lead to its end use. For example, the ligand can be an ioniccally functional material containing ionic functional groups. In that event, the resultant adduct article may be utilized in ion exchange type applications. Suitable ionic groups include carboxylic acid, sulfonic acid, phosphonic acid, tertiary amine, and quaternary amine groups. Examples of useful ionic group containing ligands include aminocarboxylic, sulfonic, or phosphonic acids such as glycine, alamine, leucine, valine, β-alamine, 8-aminobutyric acid, 1- and 3-aminopropyl-phosphonic acid, taurine, 8-amino octanoic acid, aminomethylphosphonic acid, amino-methanesulfonic acid, and the like; hydroxy-acids such as isethionic acid, 3-hydroxypropane sulfonic acid, lactic acid, glycolic acid, hydroxymethylphosphonic acid, p-hydroxybenzoic acid, and the like; and amino- and hydroxy-functional tertiary and quarternary amines such as 2-diethylaminoethylamine, 3-dimethylaminopropylamine, N,N-diethylethanol-amine, and the like, and quaternized versions thereof. When the amine-, alcohol-, or mercaptan-functional ligand is a simple aliphatic and/or aromatic hydrocarbon, the resultant adduct article may be useful in reverse phase or hydrophobic interaction type chromatographic processes. Reaction of the composite article of this invention with very hydrophilic or hydrophobic ligands can be used to produce adduce articles displaying highly absorbant properties towards aqueous or oily fluids, respectively. Other types of ligands and uses will be obvious to one skilled in the art and are considered to be within the scope of the present invention.

Objects and advantages of this invention are further illustrated by the following examples, but the particular materials and amounts thereof recited in these examples, as well as other conditions and details, should not be construed to unduly limit this invention.

EXAMPLES

Comparative Example 1

Preparation of a polytetrafluoroethylene (PTFE) porous matrix embedded with azlactone-acrylamide hydrophilic beads.

This example shows that large clumps of azlactone-functional hydrophilic beads can be incorporated into a PTFE matrix in which the clumps have been broken into their individual constituent beads. Underivatized beads were prepared according to the teachings of Example 18, U.S. Pat. No. 4,871,824, from a monomer mixture of 58 parts methylene-bis-acrylamide (MBA) and 42 parts vinyldimethylazlactone (VDM) by weight. They consisted of 100–500 $\mu$m irregular clumps of smaller (5–30 $\mu$m), spherical beads.

These beads (1 g) were processed into PTFE composites at 40° C. using a bead-to-PTFE ratio of 90:10 and ethyl alcohol as the solvent as described in U.S. Pat. No. 4,565,663. The resulting composites, totaling 50 sq. in. (323 cm$^2$), were intact, smooth, and easily handled.

SEM photographs of these composites showed that the clumps had been broken into their constituent single beads. Each bead was incorporated into and connected with the PTFE web, and they were substantially, evenly distributed throughout the composite. Most beads had dimple marks which were suggestive of a scar left after the break-off of an individual bead from a larger clump. IR spectra indicated that the azlactone group was substantially hydrolyzed during the membrane-making process. However, if it is desired to use an intermediate activation step, the azlactone group was easily recycled by the composite warming in acetic anhydride.

Example 2

Preparation of composite from pre-derivatized beads.

In this example, a composite material was prepared using Protein A-coupled beads which retained activity to bind antibody. 1.0 g of azlactone beads of Example 1 was reacted at ambient temperature (22° C.) for 1 h with 20 ml of 2.5 mg/ml of Protein A (Genzyme Corp.) in 25 mM sodium phosphate/150 mM NaCl buffer, pH 7.5. After centrifugation and removal of the supernatant solution the unreacted azlactone rings were opened by reaction for 30 min with 0.5 M ethanolamine, pH 7.5. This step was repeated followed by 4 rinses with the phosphate/NaCl buffer and 4 rinses with water. After the final centrifugation the beads were resuspended in 20% ethanol and stored overnight at 4° C. The next morning they were resuspended in 50% ethanol and then 100% ethanol, from which the PTFE composite was prepared as described in Example 1 except that the ratio of bead-to-PTFE was 80/20 weight/weight. Immediately after preparation the composite was stored under vacuum to remove the excess alcohol.

The binding of radiolabeled (I-125) bovine immunoglobulin G, IgG, (Calbiochem) which was iodinated using Iodo-Beads (Pierce) was tested using nine replicate 0.64 cm (quarter-inch) circular punches of the composite which varied from 8.0 to 9.5 mg each. The procedure employed is described in Coleman et al., *J. Chrom.*, 512, 345–363, 1990, which is incorporated herein by reference. Each sample was incubated for 1 h with 500 $\mu$l of IgG (250 $\mu$g/ml, 1700 cpm/$\mu$g, in the phosphate/NaCl buffer), and rinsed twice with buffer. The composites were blotted and transferred to a new tube, and radioactivity was determined on a Packard Model 5230 gamma scintillation counter. 2.25 Mg IgG bound per g of matrix embedded bead, approximately twice as much as a control composite prepared from beads derivatized with bovine serum albumin.

Example 3

Azlactone-functional beads (prepared from 42 parts by weight vinyldimethylazlactone (VDM) and 58 parts MBA according to the teachings of Example 25A of EP 0 392 735) were incorporated into a PTFE matrix as described in Example 1 except that tert-butanol rather than ethanol was utilized. The resultant composite was dried in a vacuum desiccator to remove the liquid.

The direct, covalent coupling of Protein A was determined using radiolabeled (I-125) Protein A similar to the IgG experiment in Example 2. Composite disks were incubated with 500 $\mu$l of Protein A solution (250 $\mu$g/ml, 2000 cpm/$\mu$g, in the phosphate/NaCl buffer) for 1 h, quenched at pH 9.0 in 3.0 M ethanolamine for 30 min., then rinsed in buffer 4 times. Radioactivity was determined after the rinsed disks were blotted and transferred to a new test tube. After standing overnight the disks were incubated with 500 $\mu$l of a 1% aqueous sodium dodecylsulfate (SDS) solution for 4 h at 37° C. and rinsed three times with 1% SDS before determining the residual radioactivity.

A control set of azlactone bead composites was treated identically except that they were initially reacted with the ethanolamine quenching agent (3.0 M, pH 9.0, 30 min) and rinsed three times prior to the incubation with the radiolabeled protein. The additional sets of controls consisted of identical beads not embedded in the composite which were reacted with radiolabeled protein, one set of which was preincubated with tert-butanol before reaction with the protein. All experiments were run in triplicate and the results were averaged.

TABLE 1

The Covalent Coupling of Protein A to Azlactone Beads and Azlactone Beads within PTFE Composites

| Sample | Protein Bound (mg/g bead) | SDS Resistance (% remaining) |
|---|---|---|
| Beads (Control) | 1.10 | 96.3 |
| Beads-alcohol (Control) | 1.29 | 95.2 |
| PTFE composite | 0.75 | 83.2 |
| Composite-amine (Control) | 0.05 | 33.7 |

These results show that the beads were still very reactive after the composite milling process. A 15-fold increase was observed in the covalent coupling of Protein A to the composite beads above that in the pre-quenched (composite-amine) control. Furthermore, the yield was 60% of that observed in unencumbered beads (the alcohol pre-treated control beads), and over 80% of the protein was covalently coupled as assessed by the SDS experiment.

Example 4

Underivatized azlactone copolymer beads were prepared by dispersion polymerization from a monomer mixture of 20% (weight/weight) VDM and 80% trimethylolpropanetrimethacrylate (TMPTMA) using the general procedure of Example 5 of European Patent Publication 0 392 735. The beads were processed into a PTFE composite at 40° C. using a bead to PTFE ratio of 90:10 (weight/weight). The resulting composite, totaling 220 sq. cm., was smooth and easily handled. The material was stored desiccated at room temperature.

To quantitate Protein A coupling to the composite incorporating azlactone beads, 0.64 cm (¼ inch) disks were punched from the previously prepared material and weighed. Triplicate disks were exposed to 0.5 mL 125-I-labeled recombinant Protein A (rProt A from Repligen) containing either 125 µg or 2.5 mg protein in phosphate-buffered saline (PBS: 0.15 M NaCl in 25 mM sodium phosphate, pH 7.5), or in 1.5 M sodium sulfate in 25 mM sodium phosphate, pH 7.5. The disks were incubated at room temperature for 60 minutes, with the initial 15 minutes under vacuum to eliminate trapped air. The reaction was terminated by removal of the protein solution and addition of 1.0 mL ethanolamine, pH 9.0, for 30 minutes, followed by a second identical treatment with fresh reagent. After several rinses with PBS, the disks were blotted and transferred to clean tubes for counting in a Packard Model 5230 Gamma Scintillation Spectrometer. The disks were subsequently treated with 1% sodium dodecylsulfate (SDS) for 4 h at 37° C. to remove non-covalently bound protein. The results of this coupling experiment are shown in Table 2. For comparison, beads of the identical polymerization were exposed to Protein A in the same buffers, including 0.1% Triton™ X-100 surfactant, with the identical coupling time, quenching conditions, and rinses.

TABLE 2

Coupling of Recombinant Protein A to Azlactone Beads, and to Beads Embedded in PTFE Matrix

|  | Beads | | PTFE + Beads | |
| --- | --- | --- | --- | --- |
| Condition | rProt A Bound (mg/g) | SDS Resist (%) | rProt A Bound (mg/g) | SDS Resist (%) |
| PBS, 0.25 mg/mL | 1.2 | 96 | 3.3 | 86 |
| Sulfate, 0.25 mg/mL | 3.5 | 98 | 1.7 | 85 |
| PBS, 5.0 mg/mL | 5.0 | 89 | 14.4 | 84 |
| Sulfate, 5.0 mg/mL | 16.6 | 97 | 11.2 | 85 |

The results shown above indicate that the azlactone beads within the PTFE composite were readily derivatized to a Protein A density greater than that of the beads alone, in the PBS buffer. Thus, formation of the composite did not adversely affect the chemical reactivity of the beads. In the presence of sodium sulfate, the Protein A capacity of the matrix-bound beads was diminished to some degree, but functionality of the beads was still demonstrated. The SDS resistance (a measure of covalently coupled protein) decreased by approximately 10% when they were in the composite, but this may have been due to the presence of PTFE which provided a very large surface area for protein adsorption. This example illustrates that azlactone beads milled into a PTFE composite retained their avidity for protein coupling, and was derivatized easily within the matrix of the composite.

Example 5

Adsorption and Elution of IgG From Immobilized rProt A on Azlactone/PTFE Composite.

25 mm disks of the composite of Example 4 were cut with a scissors and inserted into a Millipore Swinnex™-25 filter unit housing. With 5.0 mL syringes attached to both the inlet and outlet ports, 3.0 mL of rProt A solution at 5.0 mg/mL in 0.5 M carbonate buffer, pH 9.3, were injected onto the membrane, and passed back and forth through the composite for a total of 20 passes, plus an additional incubation of 30 minutes at room temperature. The reaction was terminated by removal of the protein solution, and injection of 5.0 mL of 3.0 M ethanolamine, pH 9.0 (20 passes). This reagent was then removed and fresh reagent was incubated in the composite for 30 minutes. After the quenching reaction was complete, the following rinse steps were performed: a) PBS, 5 mL (3 passes) for each of three aliquots; b) 1.0 M NaCl, 5 mL (3 passes) for each of three aliquots; c) 0.1 M glycine+2% acetic acid, pH 2.2, 5 mL (3 passes) for each of three aliquots; and d) PBS, 5 mL (3 passes) for each of three aliquots.

After covalent coupling of the ligand to the composite, the activity of the immobilized Protein A was evaluated by passage of 5.0 mL of human IgG (Sigma Chem. Co.) at 1.0 mg/mL in PBS through the composite. After ten reciprocating passes through the membrane and an additional 5 minute incubation, the protein solution was removed. The composite was rinsed free of non-bound IgG by injecting PBS in one mL aliquots, with collection of 1.0 mL fractions for analysis. After 10 mL of PBS, 5×1.0 mL of 0.1 M glycine+2% acetic acid, pH 2.2, were injected in a like fashion, but at timed intervals to effect a flow rate of 1.0 mL/min. Eluted fractions (1.0 mL) were collected. An additional 10 ml PBS were then injected for reequilibration at pH 7.5.

Fractions were evaluated for IgG concentration by absorbance readings at 280 nm. The resulting elution profile showed that 1.08 mg of IgG was specifically adsorbed and eluted from the PTFE-azlactone bead disk, compared to 0.13 mg IgG from a Nalge" disk (Nalgene Co., Rochester, N.Y.) prepared according to the manufacturer's instructions. A control PTFE-azlactone disk derivatized with only buffer (prior to the ethanolamine treatment) showed no non-specific IgG adsorption.

Example 6

Separation of IgG From Human Serum.

The actual usefulness of the type of device described in Example 5 is in separation of IgG from other components in a milieu of proteins, be it serum, culture medium, or ascites fluid. The composite used in Example 5, having azlactone-functional reactive particles derivatized with rProt A, was stored in the filter housing unit in PBS at 4° C. for seven days between uses. For further evaluation, human serum was diluted (2 mL serum+8 mL PBS) and filtered through a 0.2 µm filter (Nalgene Co., Rochester, N.Y.) for clarification. 5.0 mL of this sample were injected onto the PTFE-azlactone disk, with injection and incubation as listed in Example 5 above. In addition, 5.0 mL of 1.0 M NaCl in 25 mM phosphate, pH 7.5, and 5.0 mL of PBS followed the initial PBS rinse to remove non-specifically adsorbed serum proteins. Elution was effected with the glycine-acetic acid buffer as before. A total of 1.21 mg of human IgG from serum were eluted from the PTFE-azlactone disk, compared with 0.17 mg IgG eluted from the Nalge™ membrane of the same diameter and configuration. This Example 6 thus illustrates affinity separation and purification of an analyte from a biological fluid.

Example 7

Preparation of Microporous Polyethylene/Azlactone-functional Bead Composite Membrane Using Thermally Induced Phase Separation Techniques.

A high density polyethylene (HDPE) membrane containing 20:80 (w/w) VDM/TMPTMA beads was prepared by first dispersing the beads (5 to 15 micrometer particle size having about 0.25 meq of azlactone functional groups per g of bead) in white mineral oil having a density of 0.87 g/cc using SPAN™ 85 surfactant (ICI). The dispersion was prepared by slowly sifting small amounts of VDM beads into a mixture of 1.00 g of SPAN 85 and 100.0 g of oil using a Dispersater™ mill operating at 2000 to 2500 rpm. This device is a high speed shear mill having a disc blade impeller and is available from Premier Mill Corporation, Temple, Pa. The speed was increased to 2500 to 3000 rpm momentarily to break up lumps.

A closed metal can containing 10.0 g of the above dispersion and 42.5 g of HDPE (GM 9225 from Himont) was heated to 300° C. on a hot plate. The can was opened occasionally to stir the mixture. A similar can having 10.0 g of HDPE and 40.0 g of oil was heated at the same time under the same conditions to determine the time needed to dissolve the HDPE and obtain a homogeneous mixture. Some of the molten mixture was transferred to a pressing plate which was heated to 180° C. using a hot plate and then placed into a platen press which was heated to 180° C. After compression to a thickness of 0.5 mm (20 mil) for 2 min., the plates were removed and plunged into a container of water at room temperature.

The oil was washed out of the resultant films by submerging them in a pan containing 1,1,1-trichloroethane. This procedure was repeated three times using fresh solvent each time. Differential scanning calorimetry indicated that the resultant microporous film contained 23.4% VDM beads by weight. The size of the beads were determined by SEM to be between 0.1 and 0.3 micrometer and that they usually occurred in agglomerates of 20 to 25 micrometers. An Fourier Transform Infrared (FTIR) spectrum (background FTIR spectrum of HDPE subtracted) obtained on a piece of film which was pressed at 180° C. in order to clarify it agreed closely with a reference spectrum for the VDM beads.

Protein coupling to this composite could be deminstrated by a procedure similar to that used in Example 4.

Example 8

Preparation of non-woven webs loaded with azlactone-functional beads.

An azlactone-functional polymer bead was prepared from a 20:80 weight/weight monomer mixtures of VDM and MBA by a procedure similar to that described in Example 4E of EP 0 392 735 A2. The beads were ground in a ball mill and the fraction possessing a particle diameter of less than 37 micrometers was separated by use of a screen. The greater than 37 micrometer fraction of these directly covalently reactive particles were loaded into a polypropylene blown microfiber web. The polypropylene fibers were of 3 micrometers in diameter and the particle to web ratio was 1:1 by weight. The composite was immediately calendered between heated rolls as described in Example 1 of U.S. patent application Ser. No. 07/776,098 (Attorney's Docket 4778USA5A), now abandoned in favor of U.S. patent application Ser. No. 07/929,985 to reduce the void volume to approximately 50%.

Example 9

Coupling of proteins to particle-loaded non-woven composite.

Bovine serum albumin (BSA), human immunoglobulin G (IgG; both products of Sigma Chemical Co., St. Louis, Mo.), and recombinant Protein A (rProt A; Repligen, Cambridge, Mass.) were iodinated using sodium I-125 (New England Nuclear, Billerica, Mass.) and Iodo-Beads™ (Pierce Chemical Co., Rockford, Ill.) using the procedure of Holmes et al. *Proc. Nat. Acad. Sci.,* 1985, 82, 7706. 0.64 cm disks (prepared using a standard office paper punch) of the particle-loaded and particle-free control webs described in Example 8 were incubated with 250 μl of the radioiodinated proteins in 25 mM sodium phosphate, 150 mM NaCl, pH 7.5 (PBS) at ambient temperature with continuous mixing for 1 h. Protein concentrations were 0.1, 1, and 5 mg/ml with specific radioactivities approximating 10000, 3000, and 1000 cpm/μg, respectively. Non-radiolabeled protein was used to adjust the specific radioactivities and protein concentrations.

Following the reaction the solution was removed from the test tube and 500 μl of 1.0 M ethanolamine, pH 9.0, was added, and allowed to react with mixing for 30 min to inactivate the remaining azlactone functionality. The steps were repeated with fresh ethanolamine to ensure a complete reaction. All disks were rinsed three times with the PBS (total of 90 min), blotted on absorbent paper, and transferred to a clean 10×75 mm test tube and placed in a Packard Model 5230 AutoGamma Spectrometer (Downers Grove, Ill.) to determine incorporated radioactivity.

Evaluation of the degree of covalent protein coupling was determined by removal of non-covalently bound protein via sodium dodecylsulfate (SDS) denaturation. Each disk was incubated in 500 μl of a 1% (w/v) SDS solution (in 25 mM sodium phosphate, pH 7.5) at 37° C. for 4 h, followed by three 500 μl rinses of the disk with fresh SDS solution and repeat of the radioactivity determination. Higher retentions of radioactivity indicate higher amounts of covalent bond formation between protein and the solid phase.

In some experiments, as another means of determining the contribution of the azlactone to the protein covalent coupling, the disks were reacted with the ethanolamine solution (16 h) prior to reaction with the radiolabeled protein solution. All experiments on particle-containing webs were performed in triplicate; all those on particle-free control webs were in duplicate. Resulting data were averaged.

The results of the concentration-dependency experiments for each protein are presented in Table 3. The maximum observed for BSA and rProt A were 13–15 μg/cm$^2$, and the maximum for IgG was greater than 350 μg/cm$^2$. All concentration-dependencies were linear with no indication of saturation, suggesting that considerably more of each protein would be capable of coupling.

TABLE 3

Concentration Dependence of Protein Coupling

| Offered | Coupled Protein (micrograms/cm²) | | |
|---|---|---|---|
| Protein (mg/ml) | IgG | BSA | ProtA |
| 0.1 | 3.2 | 0.72 | 0.42 |
| 1.0 | 39.3 | 4.32 | 3.98 |
| 5.0 | 354 | 13.0 | 15.2 |

TABLE 4

Summary of Protein Coupling

| Protein | Initial Control Coupling ($\mu g/cm^2$) | Quenched Composite Coupling ($ug/cm^2$) | Initial Composite Coupling ($\mu g/cm^2$) | SDS Resistance (%) |
|---|---|---|---|---|
| rProt A | 0.16 | 2.1 | 15 | 81 |
| BSA | 0.41 | 2.2 | 13 | 71 |
| IgG | 0.25 | 2.1 | 354 | 72 |

Table 4 summarizes some additional important coupling parameters determined from the experiments performed at 5 mg/ml. Especially significant are the ratios of the initial coupling to the composite vs. the control webs. This ratio was 94, 32, and 1416, for rProt A, BSA, and IgG, respectively, indicating that practically all of the protein coupling was due to the bead portion of the composite. A low and consistent value for binding to the pre-quenched composites, about 2 $\mu g/cm^2$ was observed. For each protein at least 70% of the bound protein was covalently linked.

The disks were rugged, holding up well to the rigorous handling and continuous mixing they were subjected to during the 4 h of experimentation.

Example 10

Biological activity of Protein A immobilized on an azlactone-bead-containing composite.

A filtration device was fashioned by placing one ply of a 25 mm diameter disk of the Example 8 composite into a Swinnex-25 filter unit (Millipore Corp., Bedford, Mass.) and coupling syringes to both outlet ports of the filter unit. The syringes were used to pass solutions back and forth through the composite in a reciprocating manner.

rProt A was coupled to the composite by 20 passes of a 3 ml solution (5 mg/ml in the 0.5 M $Na_2SO_4$, 0.2% Triton X-100 surfactant, 25 mM sodium phosphate, pH 7.5) plus an additional 30 min static incubation; all steps were at ambient temperature.

The coupling reaction was terminated by removal of the protein, and injection of 1.0 M ethanolamine quencher, pH 9.0 (20 passes). Fresh quenching solution was then added and allowed to incubate for 30 min. After quenching, the filter was washed successively with: 1) PBS; 2) 1.0 M NaCl, 25 mM sodium phosphate, ph 7.5; 3) 0.1 M glycine, 0.2% acetic acid, pH 2.2; 4) PBS. All washes were three repeats of 5 ml of sample, 3 passes per repeat.

Activity of the bound rProtA was assessed by passing 5 ml of human IgG (1 mg/ml in PBS) through the membrane unit. Total residence time was 15 min. The filter was rinsed with PBS followed by 1.0 M NaCl in the phosphate buffer. IgG was eluted using the glycine-acetic acid solution, and IgG concentrations were determined by absorption at 280 nm, using 1.3 ml-cm/mg as the extinction coefficient.

As a control, all the above procedures were performed in parallel on a particle-free web. Approximately ten-fold more IgG was recovered from the bead-containing filter than the control (312 $\mu g$ vs. 34 $\mu g$). Total recovery of IgG was 101% and 96%, for the composite and the control, respectively. Using the IgG density determined in Example 9, the apparent molar ratio of IgG to rProt A was 1.26, higher than the average of about 1.0 for most examples of Protein A immobilized to a particle alone.

There was no back pressure associated with the manual passage of any of the fluids through the filters. Upon inspection following the experiment, the filter was whole with no sign of wear or fraying.

Example 11

Billet preparation.

Directly covalently reactive particle-loaded nonwoven billets were prepared by mixing 5 grams of polypropylene blown microfibers with 0–5 grams of the less than 37 micrometer reactive particles of Example 8, dry blending for 5–15 seconds in a Waring blender, carefully filling a metal mold approximately 8 cm. in diameter with the mixture, and pressing in a platten press at room temperature (about 22 degrees C.) under 10–18,000 psi (68.9–124×10⁶ $N/m^2$). The billets obtained were about 1.25–3.80 mm thick and had void volumes of 20–50%. Microfibers from 1–20 micrometers in diameter and reactive particles of 1–150 micrometers average diameter were usable. Control billets were prepared from microfibers without the addition of particles.

Example 12

Preparation of two-ply and three-ply "sandwich" composites.

Sandwich composites were prepared by first preparing a typical polypropylene blown microfiber web, sprinkling reactive particles on top of the web, placing another polypropylene web on top of the particles, then calendering this sandwich at 225° C. and 90 psi to produce a 2-ply composite. A 3-ply composite was prepared similarly by adding a second layer of particles and a third nonwoven web prior to calendering. The reactive particles utilized were the greater than 37 micrometer fraction of Example 8 and were loaded at 50 weight % of the tital composite. The 2-ply sandwich had a caliper of 0.10 mm and a 10 cc Gurley of 30 seconds. The 3-ply composite had a caliper of 0.14 mm and a 10 cc Gurley of 108 seconds. Control 2- and 3-ply sandwiches without particles were also prepared.

Example 13

Direct covalent coupling of protein to particle-loaded billets and sandwich composites.

Protein was coupled to the composites of Examples 11 and 12 and residual azlactones were de-activated with ethanolamine in the same manner as described in Example 9. rProt A was 1 mg/ml in 25 mM sodium phosphate, 25 mM sodium pyrophosphate, 1.5 M $Na_2SO_4$, pH 7.5. A rat monoclonal antibody (MAb), anti-mouse IgG2 (American Type Culture Collection, Cat. No. HB-90, Rockville, Md.) radioiodinated by the same procedure as Example 9, was incubated at 1 mg/ml in the phosphate-pyrophosphate buffer, except that sulfate was 0.75 M and pH was 9.0.

0.64 cm disks of the sandwich composites were used, and 5 mm disks of the billets were prepared using a No. 2 cork borer. Sandwich disk experiments used 200 $\mu l$ of the protein solutions; billets used 500 $\mu l$. Pre-quenching of the materials was accomplished by 16 h incubation with 500 $\mu l$ (sandwich) or 1000 $\mu l$ (billet) of 1.0 M ethanolamine, pH 9.0, with continuous mixing. Specific protein radioactivities were 1890 cpm/$\mu g$. Control (particle-free) materials were also investigated in parallel. All experiments were performed in triplicate. Results are listed in Table 5. Billet No. 6 contained a 50% by weight loading of azlactone particles, and had a caliper of 3.8 mm and a 10 cm$^3$ Gurley of 189 seconds. Billet No. 14 contained 16.7% by weight loading, a caliper of 2.54 mm, and a 10 cm$^3$ Gurley of 13 seconds.

TABLE 5

Summary of Protein Binding Experiments to Billet and Sandwich Composite Materials

| | rProt A | | MAb | |
|---|---|---|---|---|
| Material | SDS Resistance (%) | Residual Protein (μg/disk) | SDS Resistance (%) | Residual Protein (μg/disk) |
| Billets | | | | |
| No. 6 Q* | 12 | 0.8 | 4.5 | 0.4 |
| No. 6 | 28 | 10.8 | 40. | 17.0 |
| No. 14 Q* | 24 | 13.9 | 29. | 16.7 |
| No. 14 | 78 | 116. | 79. | 106. |
| Sandwiches | | | | |
| 2-ply Q* | 5.9 | 0.2 | 7.5 | 0.4 |
| 2-ply | 66. | 3.O | 51. | 1.7 |
| 3-ply Q* | 5.5 | 0.6 | 7.5 | 0.6 |
| 3-ply | 61. | 8.8 | 71. | 10.9 |

*these samples were reacted with ethanolamine before addition of protein

As with the previous composites, these demonstrate high direct covalent coupling attributable to the azlactone-functional reactive particles. In addition, the enhancement ratio (binding to particle-loaded vs. control webs) was 6- to 7-fold for the billets and 2-ply sandwiches and 35-fold for the 3-ply. Each of these results indicates that the azlactone-functional reactive particles survived the manufacturing process without significant loss in functionality.

Example 14

Preparation of a composite of azlactone beads with a ternary blown microfiber of polyester-polyethylene-polybutylene.

A nonwoven composite was prepared by the method of Example 8 using a mixture of 65% by weight polyester/polyethylene bicomponent fiber and 35% by weight polybutylene as the web forming material and the reactive azlactone-functional particle of Example 4. The composite was 11% by weight reactive particles. A bead-free control was also prepared.

Example 15

Protein coupling to a composite of azlactone beads and a ternary blown microfiber web.

All solutions and procedures were identical to those described for the sandwich composites in Example 13.

TABLE 6

Summary of Protein Coupling Experiments to the Ternary Composite

| | rProt A | | MAb | |
|---|---|---|---|---|
| Sample | SDS Resistance (%) | Residual Protein (μg/cm$^2$) | SDS Resistance (%) | Residual Protein (μg/cm$^2$) |
| Quenched | 25 | 4.2 | 16 | 2.1 |
| Experimental | 70 | 20.7 | 47 | 6.4 |

For each protein, the ethanolamine quenching step greatly reduced the amount of protein which remained following the SDS treatment, indicating that the azlactone functionality had survived the composite preparation process. In each case the amount of protein loading onto the control web (without reactive bead particles) was below that of the pre-quenched composite, as has been shown for all the other composites described in prior examples. The enhancement ratio (bead composite coupling vs. bead-free control) was three- to ten-fold.

Example 16

Demonstration of a human IgG assay of potential use in a diagnostic device using a composite article of an azlactone-functional reactive particle incorporated into a non-woven web matrix.

In this example an analyte and a control reagent are immobilized to a support. An antibody was used to probe the support for functional analyte. Binding to the control material was indicative of non-specific activity, poor washing, etc. The larger the difference in signal between the experimental and the control the greater was the potential sensitivity of a composite immunoassay developed.

In this case the analyte was human IgG; the analyte control was BSA. The probing antibody was sheep antibody raised against human IgG. The antibody had been coupled to horseradish peroxidase which, by its activity, signaled the presence of the antibody, in the same way that radioactivity signaled coupled protein in the previous examples. Peroxidase activity was determined by oxidation of o-phenylene diamine to a colored product.

The support materials used were the plied composites of Example 12 and the ternary materials of Example 14. Triplicate 0.64 cm disks of the composite and control (no reactive particles) materials were incubated with 500 μl of human IgG (1.0 mg/ml, 25 mM sodium pyrophosphate, 0.75 M Na$_2$SO$_4$, pH 9.0) with mixing for 2 h at ambient temperature. For IgG-free controls, a BSA solution in the same buffer was incubated with the composites and control materials. After the incubation, the solution was removed and rinsed for 5 min with 1000 μl PBS; following its removal 500 μl of the quenching agent (1.0 M ethanolamine and 1.0 mg/ml BSA in the pH 9.0 pyrophosphate buffer) was added, and the tubes were mixed overnight at ambient temperature. After removal of the quenching solution the disks were rinsed three times with 1000 μl of PBS with mixing between rinses for a total rinse time of 2 h. Each disk was blotted on absorbent paper prior to the immunoreaction.

Each disk was incubated with 1000 μl of a peroxidase-conjugated IgG (sheep anti-human IgG conjugated to horseradish peroxidase (HRP), from Cappel Co., Malvern, Pa.). After 1 h the supernate was removed, and the disks were stored overnight at 4° C. in 1000 μl of PBS-Tween surfactant (0.6% Tween-2 in PBS). After storage the disks were rinsed with PBS-Tween, blotted, and transferred to a clean 12×75 mm tube.

Bound HRP activity was assayed using o-phenylene diamine (OPD) as a chromogenic substrate. 1000 μl of freshly prepared substrate (30 mg of OPD, 0.1 M sodium citrate, pH 5.0, 30 μl 30% H$_2$O$_2$, in a total volume of 50 ml) was added to each tube, rapidly mixed, and allowed to react for 1 or 3 min. The color development was quenched by addition of 100 μl of 1.0 M H$_2$SO$_4$, and the solution absorbance was determined at 490 nm. Results are listed in Table 7.

TABLE 7

Summary of Human IgG Immunoassay Results on Composites

| | HRP Activity (1000 × Absorbance 490 nm/min) | | |
|---|---|---|---|
| Sample | BSA-Treated | IgG-treated | Net Activity |
| 2-ply | 65 | 220 | 155 |
| 3-ply | 46 | 381 | 335 |
| Ternary | 174 | 1301 | 1127 |

There were small absorbance changes in the bead-free control samples but the rates were considerably less than seen in the composites.

Example 17

Coating of inorganic particles with azlactone-functional copolymers to form reactive particles.

Chromatographic grade silica beads (Silicar CC-4F™, Mallinkrodt Chemical, St. Louis, Mo.) were coated with 1% by weight of an azlactone-containing copolymer by the procedure described in Example 10 of European Patent Publication 0 392 735 (VDM-60 of said example). These directly covalently reactive particles were then processed into a PTFE porous matrix using a bead to PTFE ratio of 90:10 (weight/weight). The composite article was analyzed for Protein A coupling capacity by the procedure used in Example 3 above. Covalent coupling was found to be 10 times that of a control pre-quenched with ethanolamine.

Various modifications and alterations of this invention will become apparent to those skilled in the art without departing from the scope and spirit of this invention, for example, each of the reactive particles listed in Table A above can be incorporated into continuous, porous matrices (especially nonwoven webs) in a manner comparable to methods described in the foregoing examples with respect to azlactone-functional reactive particles. It should be understood that this invention is not to be unduly limited to the illustrative embodiments set forth herein.

What is claimed is:

1. A composite article comprising:
    covalently reactive particles incorporated within a continuous, porous matrix, said reactive particles having surfaces comprising covalently reactive functional groups capable of directly forming covalent chemical bonds with nucleophilic ligands without need for an intermediate activation step.

2. The composite article according to claim 1, wherein said covalently reactive particles are selected from the group consisting of chemically modified inorganic particles and organic polymeric particles.

3. The composite article according to claim 1, wherein said covalently reactive particles are selected from the group consisting of chemically modified agarose, chemically modified silica, copolymers of vinyl acetate, copolymers of acrylamide, copolymers of methacrylamide, and copolymers of methacrylates.

4. The composite article according to claim 1, wherein said covalently reactive functional groups are selected from the group consisting of epoxides, N-hydroxysuccinimide esters, sulfonyl esters, iodoacetyl groups, aldehyde groups, and imidazolyl carbamates.

5. The composite article according to claim 1, wherein said covalently reactive functional group is an azlactone-functional group having the formula:

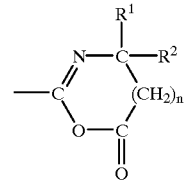

wherein
    $R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon and 0 to 3 S, N, and nonperoxidic O heteroatoms, or $R^1$ and $R^2$ taken together with the carbon to which they are joined can form a carbocyclic ring containing 4 to 12 ring atoms, and
    n is an integer 0 or 1.

6. The composite article according to claim 5, wherein said azlactone-functional group is contained in a coating on an inorganic particle.

7. The composite article according to claim 5, wherein said azlactone-functional group is present on surfaces of particles comprising copolymers including said azlactone-functional group.

8. The composite article according to claim 5, wherein said continuous, porous matrix is a web.

9. The composite article according to claim 8, wherein said continuous, porous matrix is a fibrous web.

10. The composite article according to claim 5, wherein said continuous, porous matrix is a microporous membrane.

11. The composite article according to claim 5, wherein said continuous, porous matrix is a microporous fiber.

12. The composite article according to claim 5, wherein said continuous, porous matrix is a nonwoven web having a permeable support fabric laminated to one or both sides of said nonwoven web.

13. The composite article according to claim 5, wherein said continuous, porous matrix is fibrillated polytetrafluoroethylene.

14. The composite article according to claim 5, wherein said covalently reactive particles have a size ranging from about 0.1 to about 1000 micrometers.

15. The composite article according to claim 5, wherein said covalently reactive particles are porous and when dry, have average pore sizes ranging from about 1 to 3000 Angstroms.

16. The composite article according to claim 5, wherein said covalently reactive functional group covalently couples ligands comprising biologically active material while retaining at least some biological activity.

* * * * *

UNITED STATES PATENT AND TRADEMARK OFFICE
CERTIFICATE OF CORRECTION

PATENT NO. : 5,993,935  
DATED : November 30, 1999  
INVENTOR(S) : Jerald K. Rasmussen, Steven M. Heilmann, Larry R. Krepski, Patrick L. Coleman, Dean S. Milbrath, Margaret M. Walker, Donald F. Hagen, Paul E. Hansen and John C. Campbell It is certified that error appears in the above-identified patent and that said Letters Patent is hereby corrected as shown below:

<u>Title page,</u>  
Item [54] "CONTINOUS" should be -- CONTINUOUS --.  
Item [56] References Cited, 5,155,144 is missing, should read -- 5,155,144, 10/1992, Manganaro et al., 523/134 --.  
Under FOREIGN PATENT DOCUMENTS, "92/070640" should be -- WO 92/070640 --.

<u>Column 4,</u>  
Line 68, "copolyiner" should read -- copolymer --.

<u>Column 5,</u>  
Line 19, "Siliica" should read -- Silica --.

<u>Column 12,</u>  
Line 7, insert -- ™ -- following "Iodo-Beads".

Signed and Sealed this

Twenty-eighth Day of May, 2002

*Attest:*

JAMES E. ROGAN  
*Director of the United States Patent and Trademark Office*

*Attesting Officer*